United States Patent [19]

Grosse et al.

[11] Patent Number: 4,541,424
[45] Date of Patent: Sep. 17, 1985

[54] DISTAL AIMING DEVICE FOR A LOCKING NAIL

[75] Inventors: Arsene Grosse, Strassbourg, France; Hans E. Harder, Probsteierhagen; Jürgen Klietz, Kiel, both of Fed. Rep. of Germany

[73] Assignee: Howmedica International, Inc., Kiel, Fed. Rep. of Germany

[21] Appl. No.: 466,290

[22] Filed: Feb. 14, 1983

[30] Foreign Application Priority Data

Mar. 30, 1982 [DE] Fed. Rep. of Germany ... 8208970[U]

[51] Int. Cl.⁴ .............................................. A61B 17/00
[52] U.S. Cl. ................................................. 128/92 EB
[58] Field of Search ........... 128/92 E, 92 EB, 92 EC, 128/303 R

[56] References Cited

U.S. PATENT DOCUMENTS 4,418,422  11/1983  Richter et al. ...................... 378/205

FOREIGN PATENT DOCUMENTS

| 172316 | 8/1952 | Austria | 128/92 EB |
| 482268 | 3/1938 | United Kingdom | 128/92 EB |
| 1593440 | 7/1981 | United Kingdom | |
| 762877 | 9/1980 | U.S.S.R. | 128/92 E |
| 825047 | 5/1981 | U.S.S.R. | 128/92 E |

Primary Examiner—Michael H. Thaler
Attorney, Agent, or Firm—Charles J. Knuth; Peter C. Richardson; Lawrence C. Akers

[57] ABSTRACT

A distal aiming device adapted to be connected to an x-ray apparatus is independent of the type of x-ray apparatus being used. A nail holding mechanism detachably receives the proximal end of an elongated locking nail. The locking nail is held approximately in parallel with an elongated aiming head retaining mechanism which for its part is fitted on a holding arm capable of displacement about the axis of the locking nail being held in the nail holding mechanism. The aiming head retaining mechanism carries an aiming head and is capable of displacement in a direction approximately in parallel with the axis of the nail being held in the nail holding mechanism. An adjusting pin is adapted to be accommodated by the aiming head in a direction normal to the axis of the locking nail.

10 Claims, 3 Drawing Figures

DISTAL AIMING DEVICE FOR A LOCKING NAIL

BACKGROUND OF THE INVENTION

The invention relates to a distal aiming device for a locking nail, comprising an aiming head having a bore for the accommodation of an aiming sleeve and fitted on an elongated head retaining means in such a manner that it is adjustable longitudinally of the retaining means.

Such an aiming device is known (German utility model No. 78 05 301). The aiming head retaining means is fitted in a socket which is connected to an X-ray source. The retaining means is arranged displaceably in the socket.

The aiming device serves to screw to the bone locking nails placed in the bone as in the femur or in the tibia, for example.

The openings in the bone must be bored in such a manner that they are aligned with the openings in the locking nail. Such locking nails are described, for example, in the German Utility Model No. 1 77 12 901. They are normally introduced into the bone from the proximal end and subsequently fastened (locked) in the bone by means of transverse screws.

The conventional aiming device is connected to the X-ray apparatus and is dependent thereon. Therefore, it is the object of the innovation to provide a distal aiming device for a locking nail which is independent of the type or make of the X-ray apparatus being used.

SUMMARY OF THE INVENTION

According to the innovation, this object is attained by the provision of a nail holding means for detachably receiving the proximal end of the locking nail approximately in parallel with the elongated aiming head retaining means which for its part is fitted at a holding arm capable of displacement about the axis of the interlocking nail in the nail holding means, with the aiming head retaining means detachably fitted on the holding arm and capable of displacement in a direction approximately in parallel with the axis of the nail in the nail holding means, and with two adjusting pins adapted to be accommodated by the aiming head in a direction normal to the axis of the locking nail. It is possible with the aid of the aiming device according to the innovation to perform a pre-adjustment of the aiming head relative to the locking nail. The latter is fixedly received by the nail holding means so that the main portion of the nail extends approximately in parallel with the longitudinal axis of the aiming head retaining means. For the adjustment it is necessary that the adjusting pins at the aiming head be aligned with the transverse bores at the distal end of the locking nail. For this purpose, nail holding means is capable of rotation relative to the holding arm which is adapted to be fixedly connected to the aiming head retaining means. Through relative displacement of the aiming head and the nail holding means and the locking nail, respectively, in the longitudinal direction and subsequent relative rotation the adjusting pins are adapted to be aligned with the center axes of the transverse bores in the locking nail. If, subsequently, the locking nail is driven in after having been detached from the nail holding means, and if, after the locking nail has been implanted, the nail holding means is again connected to it, the axes of the bores in the aiming head will coincide anew with the center axis of the transverse bore in the locking nail, provided the latter has not been deformed during implantation. This may be found out about by control with the aid of the X-ray apparatus, in that an aiming sleeve, for example, the axis of which coincides with the axis of an adjusting pin (which has been removed), is received in the aiming head. If no circular opening can be pictured on the monitor of the X-ray apparatus, a readjustment of the aiming head will be necessary. The readjustment is performed in the same manner as described above for the adjustment. If, now, the axis of the aiming sleee is aligned with the axis of the transverse opening, the corticalis can be center-punched and bored, respectively, via the aiming sleeve. The fitting and screwing-in of the transverse screws may be carried out in the same manner as known in connection with the setting of locking nails.

The aiming apparatus according to the invention, though likewise in need of an X-ray apparatus as in the case with the known device, is yet not restricted to a certain type but is absolutely independent thereof. The "rough adjustment", with the device according to the innovation, is performed without an X-ray apparatus and image transducer, respectively, with the latter ones serving only controlling purposes.

In one embodiment of the innovation provision is made for the nail holding means to comprise a conical section adapted to be inserted into the conical proximal end of the locking nail, and a throughbore through which a screw is passed to cooperate with an internal threaded portion of the locking nail. Known locking nails are normally provided with a conical enlargement on the proximal end and an internal thread portion on the inner surface of the conical portion for suitable instruments for the implantation of the nail. Of this feature the aiming device according to the innovation avails itself for the retention of the nail. The locking nail may be centered via the conical portion while the screw cooperating with the internal threaded portion takes care of a reproducible fixation of the locking nail making sure that it will retain its position during the process of adjusting.

According to another embodiment of the innovation provision is made for a sleeve to be connected to the holding arm having a cylindrical bearing component of the locking nail holding means supported for rotation therein but adapted to be located. It goes without saying that the axis of rotation of this rotary bearing coincides with the axis of the locking nail when the latter has been received by the nail holding means.

In another embodiment of the invention provision is made for the aiming head retaining means to be in the shape of a rod adapted to be fastened at the holding arm by means of a clamping block. The retaining rod is preferably formed of a light-weight material such as titanium, for example. It preferably carries furthermore a scale so as to enable a preadjustment prior to making the exact adjustment of the locking nail corresponding to the nail length respectively to be used. According to another embodiment of the innovation provision is made for the holding arm to be pivotally supported about an axis normal to the longitudinal extension of the aiming head retaining means. In this manner it is possible to pivot the aiming head and the aiming head retaining rod out of the way of the rays of the X-ray apparatus, in order to adjust the latter to the distal nail opening in the locking nail until the nail opening is pictured circular on the monitor. Following this, the aiming head may again be pivoted back into main path of radiation. In this connection, mention may be made of another advantage of the aiming device according to the innovation which resides in that the components to be actuated (for instance, during a procedure of readjustment) are disposed outside the zone of rays of the X-ray apparatus, so that in case of possible readjustments the latter may be left in its switched-on condition. Besides, it has no bearing on the unobjectionable operation of the aiming device whether the nail implanted in the medullary canal is distorted or bent, because the aiming device according to the innovation is universally adjustable and the aiming head may be aligned with the distal nail openings in any position.

To receive an adjusting pin the aiming head according to the innovation is preferably provided with a bore. The adjusting pin is inserted into the bore. The adjusting pin preferably is provided with an abutment formed by a shoulder, for example, limiting the introduction of the adjusting pin into the bore.

According to another embodiment of the invention there are two parallel bores provided in the aiming head for the reception of two adjusting pins. It is possible with the aid of such an embodiment of the aiming device according to the innovation to screw with the bone two distal openings immediately one after the other. After a first opening has been bored in the bone the aiming head may be located with respect to this bore with the aid of an adjusting pin, so that subsequently the second opening is bored in the outer and inner corticalis of the bone.

As the locking nail used for the tibia is angled off at the proximal end, provision is made in one embodiment of the innovation for the nail holding means to comprise a bracket-like portion for a locking nail for the tibia, the longitudinal extension of which extending in parallel with the aiming head retaining means. In this manner, it is possible also for the nail having the proximal end angled-off to be rotated about its own axis for adjusting purposes.

DETAILED DESCRIPTION OF THE INVENTION

In the following, some examples of embodiment of the innovation are going to e explained in more detail by way of drawings.

Figure 1:
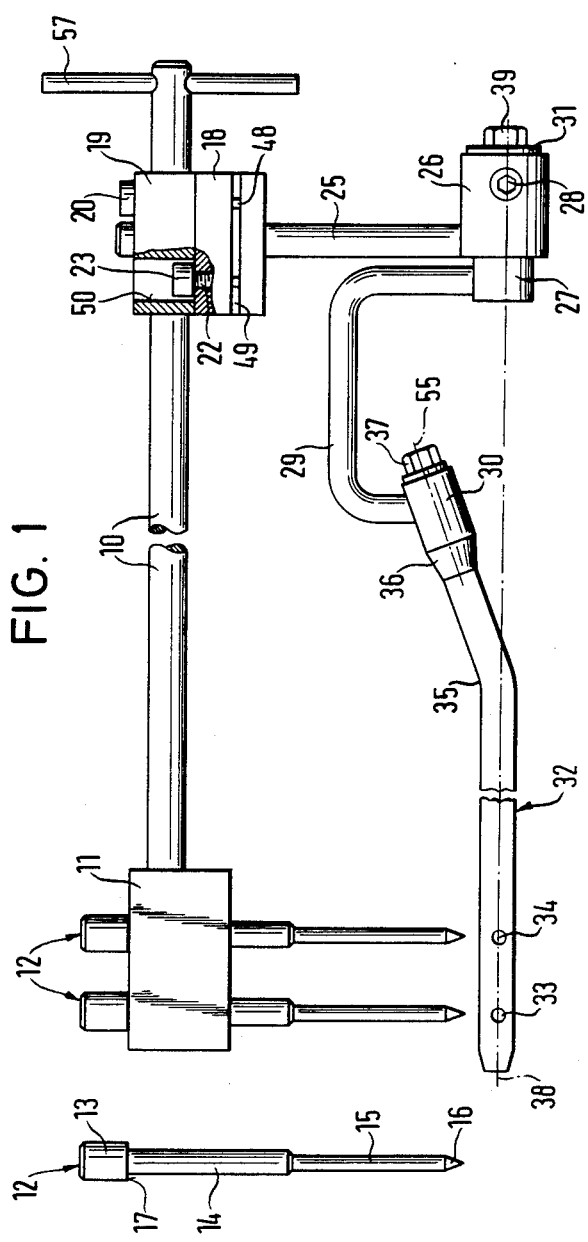
FIG. 1 shows in a diagrammatic view an aiming apparatus according to the innovation for a tibial locking nail.

Prior to enlarging in more detail on the individual representations shown in the drawings, let it be stated that each of the features shown and described is of essential importance to the innovation by itself or in connection with features of the claims.

The aiming device shown in FIG. 1 comprises a retaining rod 10, which is provided with a scale (not shown), in the form of spaced annular grooves, for example, in the outer periphery of the rod 10 which is circular in cross section. At one end of the rod 10 an aiming head 11 is arranged in the shape of a parallelepepidal block. The aiming head 11 has two parallel bores (not shown here) normal to the axis of the retaining rod. The bores serve to receive adjusting pins 12, one of them being shown laterally taken out. The adjusting pin 12 is provided with a cylindrical head 13, a shank portion 14 adjoining it as well as, adjoining the latter, a thinner shank portion 15 with a tip 16. When accommodated in the aiming head 11 the shoulder 17 formed due to the difference in diameter between the head 13 and the shank portion 14 comes to lie in close contact against the facing outer surface of the aiming head. The shank portion 14 is seated in the bore formed in the aiming head 11 with a minimum of dimensional tolerance.

At the opposite end of the retaining rod 10 a transversely extending handling rod 57 is inserted in a throughbore.

The retaining rod 10 is fastened at a clamping block 18 which is displaceable in either direction on a holding arm 25 and capable of rotary movement. The retaining rod 10 is clamped tightly to the clamping block 18 via a clamping shim 19 by means of a screw 20. The clamping block 18 is slotted at the lower end thereof in parallel with the retaining rod 10. Situated in the slot 49 is a clamping plate 47 provided with a groove engaging a shoulder of a clamping screw 23. The clamping screw 23 is countersunk in the clamping shim 19 through an enlargement 50 in diameter and is provided with a threaded shank 22 threaded into a threaded bore 21, and with a terminal abutment 24. Through rotation of the clamping screw 23 the plate 47 may be tilted upward and downward, respectively, thereby obtaining a clamping engagement of the block 18 at the holding arm 25. The clamping plate is fixed in its position by means of a pin 48.

If the clamping screw 23 is slightly loosened, the clamping block 18 together with the retaining rod 10 may be pivoted about an axis normal to the axis of the retaining rod 10 but cannot be moved axially. If the screw 23 is turned out by rotation as far as the abutment, an axial movement will be possible, too.

The retaining arm 25 slides in bores of the clamping shim 19, the clamping block 18 and the clamping plate 47.

Arranged at the other end of the holding arm 25 is a sleeve 26 which accomodates a cylindrical bearing structural member 27. The position of rotation of the bearing structural component 27 may be fixed with the aid of two screws 28 disposed exactly opposite each other and the head of which is provided with an internal hexagon. A screw 39 at the opposite end of the sleeve 26 and a disc 31 form an axial abutment for the bearing structural member 27.

Fitted at the end of the bearing structural component 27 projecting from the sleeve 26 is a C-shaped bracket 29 having a nail holding means 30 arranged at the other end thereof with the axis 55 thereof extending obliquely with respect to the axis of the holding rod 10. The nail holding means 30 serves to preliminarily fix a locking nail 32 of known-per-se construction, which is provided with two spaced transverse bores 33 and 34, respectively, at the distal end and is bent off at 35 at the proximal end and is provided with a conical enlargement 36 at the proximal end. The locking nail 32 furthermore comprises a threaded section adjoining the conical section 36. The nail holding means 30, now, has a conical portion which is not visible and which fittingly engages within the conical portion 36 of the nail 32, in order to retain the latter in a predetermined position. A screw 37 introduced from behind into a throughbore of the nail holding means 30 engages within the threaded portion of the nail 32, in order to clamp it tightly against the holding means 30. The nail holding means 30 is mounted in such a manner that the locking nail 32 fastened thereat will assume a position such that the axis 38 thereof comes to coincide with the axis of rotation of the bearing structural component 27.

The handling of the aiming device as described is as follows:

After having selected the locking nail 32 to be implanted (by diameter and length) said nail is fixedly adapted at the nail holding means 30 with the aid of the screw 37. By loosening the clamping screw 20 the retaining rod 10 now is displaced such that the corresponding measuring line on the scale of the retaining rod 10 is brought into coincidence with the corporal inner edge of the clamping block. Subsequently, the clamping screw 20 is slightly tightened again.

Following this, the adjustment is performed in the plane of rotation. For this purpose, the screws 28 are loosened in the sleeve 26 to such a degree that the arm 25 together with the retaining rod 10 may be easily rotated about the axis 38 of the nail 32. Two adjusting pins 12 bearing the inscription "T5" (in case of femur "F6") are inserted into the corresponding bores of the aiming head 11. The rotation as described is continued until the adjusting pins 12 may be pushed through the distal bores 33, 34 of the nail 32 without tension. If an elongated alignment is not yet given, the necesssary re-adjustment must be effected by relative displacement of the retaining rod 10 and the clamping block 18 (as described above). Following this, the screws 20 and 28 are again fastly tightened. For the implantation of the nail 32, the latter is removed out of the pre-adjusted aiming device by pulling out the adjusting pins 12 and loosening the retaining screw 37. The implantation of the nail is carried out as usual. For distal locking the pre-adjusted aiming device is again screwed to the implanted nail 32 by means of the retaining screw 37. By loosening the screw 23 the retaining rod 10 together with the aiming head 11 may be pivoted about the axis of the holding arm 25 and tightened again, whereby an X-ray apparatus may be positioned without being obstructed by the aiming device in such a manner that the distal openings 33, 34 can be pictured on the monitor to show a circular configuration. When the X-ray apparatus has been adjusted, the aiming head 11 is pivoted back into the main beam path by loosening the screw 23. Subsequently, boring sleeves or aiming sleeves (not shown) may be introduced into the bores of the aiming head 11. By means of the X-ray control it may be decided whether the aiming head owing to the nail having been bent or distorted during the process of driving-in is still in need of being adjusted. This may be recognized from the fact that with the aiming head 11 pivoted back together with the aiming sleeve no circular aperture can be produced on the monitor.

The re-adjusting of the aiming head 11 is performed stepwisely in the same manner as described above in connection with the pre-adjustment. After the stitch incision has been performed, the aiming sleeve (not shown) is pushed forward to such an extent that it comes to lie in close contact against the medial corticalis. After an X-ray control carried out anew the outer corticalis is punch-centered by means of an awl. Following this, both corticales are pierced through with a 3.5 diameter drill (in the case of a femur 4.5 diameter). Thereafter, an adjusting pin 12 bearing the inscription "T3.5" (in the case of a femur "F4.5") is pushed into and through the bore as far as through the second corticalis, whereby the aiming head 11 is fixed in its position.

Following this, the second opening will be bored with a diameter of 3.5 mm (in the case of a femur 4.5 mm), subsequently, the openings are enlarged by boring to a diameter of 5 (in the case of a femur 6 mm).

After the bores have been completed, the bone screws are normally screwed in.

Figure 2:
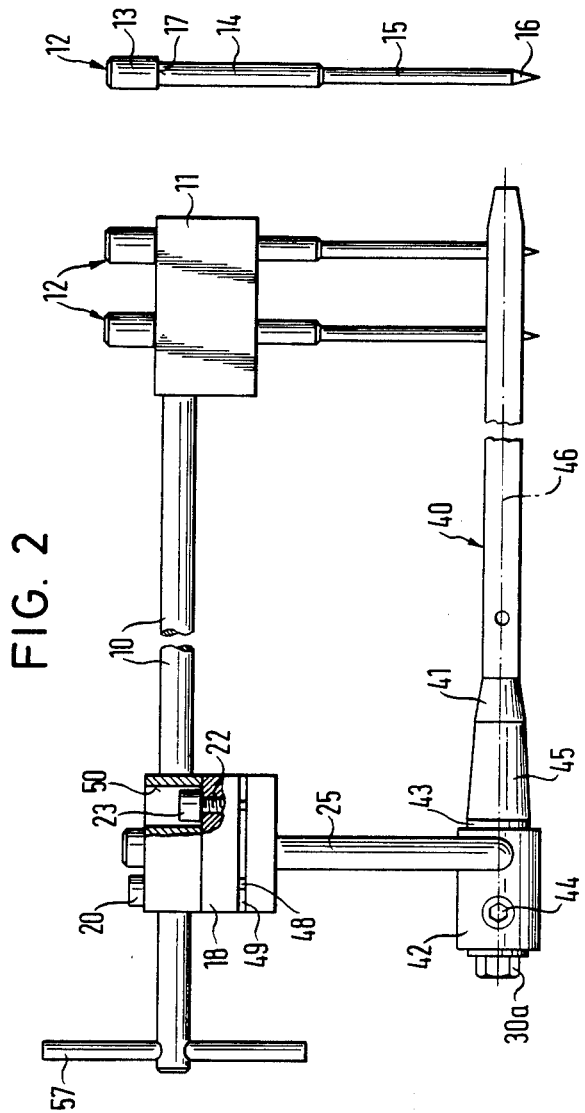
FIG. 2 shows in a diagrammatic view an aiming device according to the innovation for a femoral locking nail.
Figure 3:
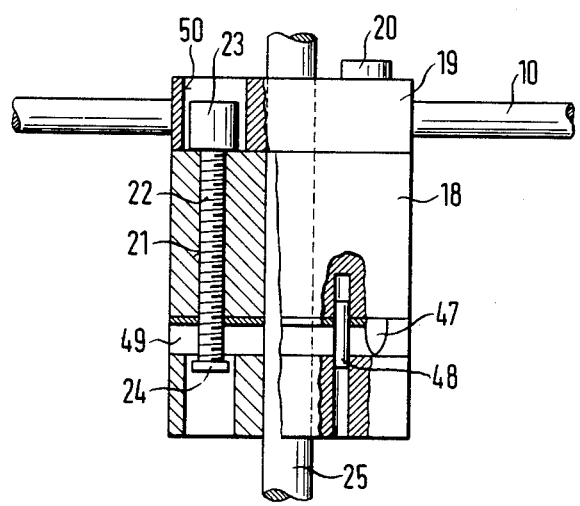
FIG. 3 shows in a diagrammatic view a clamping block used in connection with the devices.

The aiming device shown in FIG. 1 serves to lock a tibial locking nail. The aiming device according to FIG. 2 serves to lock a femoral locking nail. Besides, all the components that equal those in the example of embodiment according to FIG. 1 are provided with like reference numerals. They will also no longer be dealt with in the following. The femoral locking nail 40 is designed to be straight but also has a conically enlarged proximal end portion 41. Fastened directly to the arm 25 is a nail holding means 42 which equals the structural members 26, 27 according to FIG. 1. It is provided in the form of of a sleeve accommodating a cylindrical structural member 43 adapted to be located in its position of rotation with respect to the sleeve 42 with the aid of two screws 44. A conical adapter piece 45 is rigidly connected to the sleeve 43. The adapter piece 45 comprises a conical end portion (not shown), which is fittingly seated in the conical portion (41) of the nail 40. The threaded shank of the screw 30a extends over the conical portion 41 of the nail in the threaded portion thereof in order to fastly tighten the nail 40 against the adapter piece 45. By loosening the screw 44 the nail 40 may be rotated about its axis 46, in order to align the distal transverse bores of the nail 40 with the adjusting pins 12 in the manner as described above. The retaining rod 10 may consist of titanium, for example.

For the femur device adjusting pins bearing the inscription "F6" and "F4.5", respectively, will be used.

We claim:

1. A distal aiming device for a locking nail comprising an aiming head which is provided with a bore and is carried by an elongated aiming head retaining means, a nail holding means for detachably receiving the proximal end of the locking nail, a holding arm connected to the nail holding means and capable of rotation about the longitudinal axis of the locking nail being held in the nail holding means, said aiming head retaining means being releasably fitted on the holding arm and being capable of reciprocating displacement relative to the holding arm and the nail holding means in a direction parallel with the longitudinal axis of the nail, and an adjusting pin capable of being received by the aiming head within said bore in a direction normal to the longitudinal axis of the locking nail, with said aiming head retaining means comprising a retaining rod releasably fitted on the holding arm by means of a clamping block, said clamping block being rotatably supported on both said holding arm and said retaining rod, and said device including means to releasably lock said clamping block to said holding arm and means to releasably lock said clamping block to said retaining rod.

2. An aiming device of claim 1 wherein said holding arm includes an integral sleeve, with a cylindrical structural component of the locking nail holding means being rotatably supported within said sleeve, and said device includes means to releasably lock said sleeve to said cylindrical structural component.

3. An aiming device of claim 1 wherein said aiming head has two parallel bores for the reception of two adjusting pins.

4. An aiming device of claim 1 wherein said nail holding means comprises a bracket-like portion, the longitudinal extension of which is parallel to the longitudinal axis of the nail being held in said nail holding means.

5. An aiming device of claim 1 wherein said holding arm has a rod-like portion of circular cross section extending through a bore of the clamping block, with a slot formed in the clamping block transversely of said bore for tiltably receiving a clamping plate and with said rod-like portion extending through a bore of the clamping plate, and a clamping screw screwed into the clamping block being in engagement with the clamping plate for tiltably adjusting the clamping plate, whereby when said clamping screw is screwed into the clamping block to a first position relative translational displacement between the holding arm and clamping block is prevented but relative rotational displacement between the holding arm and the clamping block about the axis of the holding arm is permitted, and when said clamping screw is further screwed into the clamping block to a second position both relative translational displacement and relative rotational displacement between the holding arm and the clamping block are prevented.

6. An aiming device of claim 5, wherein said holding arm includes an integral sleeve, with a cylindrical structural component of the locking nail holding means being rotatably supported within said sleeve, and said device includes means to releasably lock said sleeve to said cylindrical structural component.

7. A distal aiming device for a locking nail comprising an aiming head which is provided with a bore and is carried by an elongated aiming head retaining means, a nail holding means for detachably receiving the proximal end of the locking nail, a holding arm connected to the nail holding means and capable of rotation about the longitudinal axis of the locking nail being held in the nail holding means, with said holding arm including an integral sleeve, a cylindrical structural component of the locking nail holding means being rotatably supported within said sleeve and said aiming head retaining means being releasably fitted on the holding arm and being capable of reciprocating displacement relative to the holding arm and the nail holding means in a direction parallel with the longitudinal axis of the nail, an adjusting pin capable of being received by the aiming head within said bore in a direction normal to the longitudinal axis of the locking nail, and means to releasably lock said sleeve to said cylindrical structural component.

8. An aiming device of claim 7 wherein said aiming head retaining means comprises a retaining rod releasably fitted on the holding arm by means of a clamping block.

9. An aiming device of claim 7 wherein said aiming head has two parallel bores for the reception of two adjusting pins.

10. An aiming device of claim 7 wherein said nail holding means comprises a bracket-like portion, the longitudinal extension of which is parallel to the longitudinal axis of the nail being held in said nail holding means.

* * * * *